United States Patent [19]

Durante et al.

[11] Patent Number: 5,386,074
[45] Date of Patent: Jan. 31, 1995

[54] CATALYTIC DEHYDROGENATION OF ALKANES

[75] Inventors: Vincent A. Durante, West Chester; James E. Lyons, Wallingford, both of Pa.; Darrell W. Walker, Visalia, Calif.

[73] Assignee: Sun Company, Inc. (R&M), Philadelphia, Pa.

[21] Appl. No.: 100,595

[22] Filed: Jul. 30, 1993

Related U.S. Application Data

[60] Continuation-in-part of Ser. No. 995,637, Dec. 17, 1992, Pat. No. 5,276,241, which is a division of Ser. No. 906,066, Jun. 29, 1992, Pat. No. 5,227,565.

[51] Int. Cl.⁶ ............................................. C07C 5/327
[52] U.S. Cl. .................................... 585/658; 585/621; 585/624; 585/627; 585/629; 585/654; 585/661
[58] Field of Search ................ 585/627, 658, 621, 624, 585/629, 654, 661

[56] References Cited

U.S. PATENT DOCUMENTS

| | | | |
|---|---|---|---|
| 3,792,103 | 2/1974 | Walker et al. | 585/623 |
| 4,172,810 | 10/1979 | Mitchell et al. | 252/465 |
| 5,073,657 | 12/1991 | Warren | 585/500 |
| 5,073,664 | 12/1991 | Durante et al. | 585/700 |
| 5,227,565 | 7/1993 | Durante et al. | 585/656 |

OTHER PUBLICATIONS

Patel et al., "Selective Oxidative Dehydrogenation of Alkanes over Mg Vanadates," *Proc. 9th Intern. Congr. Catalysis*, 1554–61 (1988).
Yamashita et al., "Oxidative Coupling of Methane with Peroxide Ions over Barium–Lanthanum–Oxygen Mixed Oxide", *Appl. Catalysis A: General*, 79, 203–214 (1991).

*Primary Examiner*—Asok Pal
*Assistant Examiner*—P. Achutamurthy
*Attorney, Agent, or Firm*—Q. Todd Dickinson; Stephen T. Falk

[57] ABSTRACT

Barium peroxide in which has been incorporated a transition metal compound is used as a catalyst for the oxidative dehydrogenation of organic compounds in the presence of terminal oxidants.

18 Claims, No Drawings

CATALYTIC DEHYDROGENATION OF ALKANES

This application is a continuation in part of application Ser. No. 07/995,637, filed Dec. 17, 1992, now U.S. Pat. No. 5,276,241, which was a divisional of application Ser. No. 07/906,066, filed Jun. 29, 1992, now U.S. Pat. No. 5,227,565.

BACKGROUND OF THE INVENTION

This invention relates to a method for the catalytic oxidative dehydrogenation of dehydrogenatable organic compounds.

In U.S. Pat. No. 5,073,664 issued Dec. 17, 1991, a process for the coupling of alkanes at low temperature over a regenerable stoichiometric reagent, barium peroxide, is disclosed. We have further found, as disclosed in U.S. Pat. No. 5,227,565, issued Jul. 13, 1993, that by modifying the catalyst by incorporation of transition metal complexes or salts, reactivity is significantly altered even though levels as low as 1% (wt) of a transition metal are added to the barium peroxide.

Walker et al., U.S. Pat. No. 3,792,103, disclose oxidative dehydrogenation of alkanes using Phillips' Ni/Sn/P/K catalyst at high temperatures. At 593° C. and a high air to butane ratio (gas hourly space velocities: n-butane, 500 $h^{-1}$; air, 2500 $h^{-1}$; steam, 5000 $h^{-1}$), the Phillips catalyst resulted in 39.9% conversion of butane and 62.1% selectivity to butenes plus butadiene.

Patel et al., Selective Oxidative Dehydrogenation of Alkanes over Mg Vanadates, Proc. 9th Int. Congr. Catalysis, 1554–61 (1988), discloses V/Mg/O catalysts useful for oxidative dehydrogenation of alkanes. At 540° C. with $Mg_3(VO_4)_2$ catalyst, Patel et al. report up to 17% conversion of butane, 56% selectivity to butenes and butadienes and 36% selectivity to carbon oxides.

We have now found that barium peroxide doped with transition metal compounds can be utilized not only as a regenerable stoichiometric reagent, but also as a catalyst or catalyst precursor for the continuous oxidative dehydrogenation of organic compounds in the presence of co-fed oxidants. The active catalytic species have not been identified, but are believed to form in situ.

SUMMARY OF THE INVENTION

According to our invent ion, dehydrogenatable organic compounds having three to five carbon atoms in the molecule are oxidatively dehydrogenated by contact with an oxidant and a catalyst prepared by doping barium peroxide with a compound of a transition metal from Groups IIIA through VIIIA or from Groups IB through IIB of the Periodic Table or with compounds of indium, tin, lead or bismuth. Molecular oxygen is a preferred oxidant. Other oxidants in vapor or liquid phase may also be used, such as organic peroxides, hydrogen peroxide, ozone, hypochlorite, and the like. Dehydrogenatable hydrocarbons are preferably alkanes, and more preferably isobutane.

DETAILED DESCRIPTION OF THE INVENTION

According to our invention, dehydrogenatable organic compounds are oxidatively dehydrogenated by contact in the presence of an oxidant, such as molecular oxygen, in a reaction zone over a solid catalyst prepared by doping or promoting barium peroxide with a compound of a transition metal chosen from the Groups IIIA through VIIIA or from Groups IB through IIB of the Periodic Table [Fischer Scientific No. 05-702 (1981)] or with compounds of indium, tin, lead or bismuth. Other oxidants in vapor or liquid phase may also be used, such as organic peroxides, hydrogen peroxide, ozone, hypochlorite and the like, in place of a portion or all of the oxygen-containing gas. Dehydrogenatable organic compounds are preferably alkanes and more preferably isobutane.

The temperature and pressure in the reaction zone must be sufficient to dehydrogenate the dehydrogenatable organic compound. Temperatures in the range of 250° C. to 650° C., preferably 350° to 550° C., and pressures in the range of 0 to 2000 psig, preferably 10 to 900 psig, are effective. The temperature will vary depending on the processing arrangement and the feedstock, but the minimum temperature necessary is easily determined. Suitable reactors for carrying out the process of the present invention include static or circulating fluidized bed reactors, packed bed reactors and trickle bed reactors. Other conventional reactor configurations could be used as well.

Barium peroxide is a stable article of commerce and readily available. It can also be made by the reaction of barium or barium oxide in air or oxygen at 500° to 600° C. in the presence of steam.

The catalyst, or precursor thereof, may be prepared by several techniques through which barium peroxide or its precursor compounds are doped with metal compounds. Presynthesized or purchased barium peroxide may be doped with metal by impregnation with liquid solutions of metal salts or complexes. For example, iron (II) tetrafluoroborate (aqueous), chromic nitrate, manganese (II) nitrate, or polynuclear metal complexes such as heteropolyacids (typically Keggin or Dawson structures), or other polynuclear metal species, particularly those containing iron or ruthenium and at least one labile ligand, may be used in aqueous solution and applied to a dispersed powder of barium peroxide followed by vacuum drying of the solid at 80° C. Alternatively, barium plus promoting metal salt mixtures can be co-precipitated followed by treatment with concentrated hydrogen peroxide or with oxygen at high temperature to form peroxides phases. Effective concentrations of the metal compound dopant in the catalyst are approximately 0.2 to 70 weight percent, preferably 1 to 20 wt.%, more preferably 2 to 6 wt. %. Iron is a preferred metal dopant. A variable amount of barium carbonate, barium bicarbonate, or barium oxide may also be present.

It is unlikely that peroxide species survive more than a few catalytic cycles under continuous oxidative dehydrogenation conditions below about 550° C. Consequently, the nature of the functional catalytic species in the reactor will vary depending on the reaction temperature and oxidant partial pressure utilized and the time on-stream.

Introduction of oxidant into the reaction allows for continuous catalytic oxidative dehydrogenation to occur. In the preferred temperature range of 300° to 550° C., the reaction is selective for dehydrogenation when the dehydrogenatable hydrocarbon is isobutane and the oxidant is molecular oxygen. At higher temperatures, products of oxidative coupling and cracking of coupled products are often observed, but some dehydrogenation products are also usually produced.

Suitable feedstocks for use in the invention are those which contain one or more dehydrogenatable organic compounds alone or in admixture, or in diluted form with nondehydrogenatable material such as steam, nitrogen, and the like.

Dehydrogenatable organic compounds can be characterized as containing at least one

grouping, i.e., having at least one saturated carbon-carbon bond. Compounds to be dehydrogenated according to the process of the present invention typically contain three to five carbon atoms per molecule. It is feasible to dehydrogenate suitable compounds containing a greater number of carbon atoms, although such are often not readily available commercially. Compounds to be dehydrogenated can be branched or unbranched structures.

Particularly suitable for dehydrogenation in accordance with the process of the invention are alkanes, including acyclic and cyclic hydrocarbons, particularly the former. Among the alkanes, those containing three to five carbon atoms per molecule are useful feedstocks. Preferred among these is isobutane. Mono-olefins, such as 1-mono-olefins, can be successfully dehydrogenated to a higher degree of unsaturation. Feedstocks can be relatively homogeneous, i.e., a single compound, or can be mixed feedstocks, such as those available from various refinery streams and containing a variety of compounds. The compounds to be dehydrogenated can be branched or unbranched.

The conversions of isobutane to isobutene, butanes to butenes and butadienes, isopentane to isoamylenes and isoprene, and butenes to butadienes, are accomplished through the process of the invention. Propane, isobutane, pentane, hexane, 2-methylhexane, octane, 2,4-dimethyloctane, 2-methylbutene-1, hexene-2, octene-1, 3-methylnonene, dodecane-1, and the like are components of feedstock suitable for the process of the invention.

In addition, alkylpyridines and alkylaromatic compounds containing one to four, preferably one to two, alkyl groups per molecule, wherein the alkyl groups contain from one to six, preferably two to six, carbon atoms per group and including at least one alkyl group having at least two carbon atoms, can be dehydrogenated to the corresponding alkenyl-substituted pyridines and aromatic compounds. Such alkylaromatic compounds include ethylbenzene, diethylbenzene, ethyl toluene, propyl benzene and isopropyl benzene.

Suitable oxidants for use in the invention include air, oxygen, hydrogen peroxide, organic peroxides or hydroperoxides, ozone, single oxygen atom donors (such as hypochlorite), and other oxygen donors in liquid or vapor phase. Preferred oxidants are oxygen and air. An example of an organic hydroperoxide useful as oxidant in the present invention is tertiary butyl hydroperoxide. The molar ratio of dehydrogenatable organic compound to terminal oxidant in the reaction zone should be maintained in the range of 0.05:1 to 20:1. Preferred ranges are chosen based on the specific feedstock plus oxidant combination, the reaction temperature, and a consideration of explosive potential of the feed mixtures. Steam may be optionally co-fed also as a heat transfer medium, but it is not required.

EXAMPLE

Doped barium peroxides were prepared by impregnation of purchased barium peroxide with aqueous solutions of cerium or chromium salts, followed by vacuum drying at 80° C. Metal loading in the final products was 1 weight percent.

Experiments were performed in which isobutane was passed over doped barium peroxides in the presence of an oxidant, namely air, at high pressure and at moderate temperatures in a packed bed reactor as set forth in the Table. On-line analytical systems indicated the products to be dehydrogenation (isobutene) and combustion ($CO_x$) products, as shown in the Table, infra. Results were compared to the oxidative dehydrogenation activity of the Phillips Petroleum Co. Ni/Sn/P/K catalyst taught in U.S. Pat. No. 3,790,501, and prepared according to the description therein.

Under the conditions cited in the Table, there was essentially complete consumption of oxygen, the limiting reagent. The dominant products of the reaction were isobutene and carbon oxides; no coupling products were observed and there was little fragmentation ($C_3$). The results indicate that at low pressures, the Ce-doped barium peroxide produced approximately half the selectivity for isobutene than did the Cr-doped sample. At high pressures, there was little observed difference between the dehydrogenation activity of the Cr- and Ce-doped barium peroxides.

TABLE

| Catalyst | GHSV $iC_4$ or $nC_4$ ($h^{-1}$) | GHSV Air ($h^{-1}$) | Temp. (°C.) | Press. (psig) | Time On-stream (h) | $C_4$ Conv. (mol %) | $O_2$ Conv. (mol %) | Sel $C_4$ (C at. %) | Sel $CO_x$ (C at. %) | Sel $C_3$ (C at. %) |
|---|---|---|---|---|---|---|---|---|---|---|
| Cr/$BaO_2$ | 1283 ($i$-$C_4$) | 504 | 420 ± 1 | 49 ± 1 | 2 | 6.8 | 99.7 | 57 | 40 | 3 |
| | | | | | 8 | 5.8 | 99.5 | 59 | 39 | 3 |
| | | | | | 24 | 6.3 | 99.5 | 68 | 30 | 2 |
| | | | 415 ± 1 | 850 ± 50 | 2 | 4.1 | 92.5 | 58 | 33 | 9 |
| | | | | | 8 | 3.9 | 98.4 | 59 | 31 | 10 |
| | | | | | 24 | 4.0 | 98.6 | 60 | 31 | 9 |
| Ce/$BaO_2$ | 1283 ($i$-$C_4$) | 504 | 425 ± 1 | 54 ± 1 | 2 | 5.1 | 98.8 | 32 | 62 | 6 |
| | | | | | 8 | 5.0 | 98.7 | 37 | 57 | 7 |
| | | | | | 24 | 4.4 | 98.5 | 36 | 57 | 7 |
| | | | 413 | 815 | 2 | 4.5 | 99.2 | 61 | 26 | 13 |
| Ni/Sn/P/$K^b$ | $200^c$ ($n$-$C_4$) | $1000^c$ | 461 | 132 | 2 | 17.6 | 99.9 | 21 ($C_4^=$ + $C_4^{==}$) | 76.9 | 2.1 |
| | $300^d$ | $1500^d$ | 404 | 48 | 2 | 5.3 | 11.4 | 17 | 79.4 | 3.6 |

TABLE-continued
CONTINUOUS REACTION OF ISOBUTANE PLUS AIR[a] OVER DOPED BARIUM PEROXIDES

| Catalyst | GHSV iC$_4$ or nC$_4$ (h$^{-1}$) | GHSV Air (h$^{-1}$) | Temp. (°C.) | Press. (psig) | Time On-stream (h) | C$_4$ Conv. (mol %) | O$_2$ Conv. (mol %) | Sel C$_4$ (C at. %) | Sel CO$_x$ (C at. %) | Sel C$_3$ (C at. %) |
|---|---|---|---|---|---|---|---|---|---|---|
| (n-C$_4$) | | | | | | | | (C$_4^=$ + C$_4^{==}$) | | |

[a]Packed bed reactor with on-line analytical capability; traces of oxygenated compound products were observed in all runs, but these were not included in selectivity calculations. No coupling products were observed in any run.
[b]Oxidative dehydrogenation catalyst prepared according to examples in U.S. Pat. 3,790,501, assigned to Phillips Petroleum Co., which is incorporated by reference herein.
[c]Steam, GHSV = 130 h$^{-1}$, and N$_2$, GHSV = 2000 h$^{-1}$, were also co-fed.
[d]Steam 3200 h$^{-1}$ was also co-fed.

What is claimed is:

1. A dehydrogenation process which comprises contacting an organic compound having at least one saturated carbon-carbon bond and an oxidant with a catalyst in a reaction zone under conditions sufficient to dehydrogenate said organic compound, wherein said catalyst comprises barium peroxide and compounds of metal selected from the group consisting of Groups IIIA through VIIIA elements and Groups IB through IIB elements of the Periodic Table, indium, tin, lead and bismuth.

2. The process of claim 1 wherein said metal is selected from the group consisting of iron, chromium, cerium, silvers, molybdenum, ruthenium and titanium.

3. The process of claim 2 wherein said metal comprises iron.

4. The process of claim 1 wherein said oxidant is selected from the group consisting of oxygen, air, hydrogen peroxide, organic peroxides, organic hydroperoxides, single oxygen atom donors and ozone.

5. The process of claim 4 wherein said oxidant agent comprises oxygen.

6. The process of claim 4 wherein said oxidant comprises air.

7. The process of claim 1 wherein the molar ratio of said organic compound to said oxidant is in the range of 0.05:1 to 20:1.

8. The process of claim 1 wherein said process is carried out at a temperature in the range of 250° to 650° C.

9. The process of claim 8 wherein said temperature is in the range of 350° to 550° C.

10. The process of claim 1 wherein said process is carried out at a pressure in the range of 0 to 2000 psig.

11. The process of claim 10 wherein said pressure is in the range of 10 to 900 psig.

12. The process of claim 1 wherein said organic compound comprises an alkane containing three to five carbon atoms per molecule.

13. The process of claim 12 wherein said alkane comprises isobutane.

14. The process of claim 1 wherein said reaction zone comprises a fluidized bed reactor.

15. The process of claim 1 wherein said reaction zone comprises a packed bed reactor.

16. The process of claim 1 wherein the concentration of said metal compound in said catalyst is in the range of approximately 0.2 to 70 weight percent.

17. The process of claim 16 wherein the concentration of said metal compound in said catalyst is in the range of approximately 1 to 20 weight percent.

18. The process of claim 17 wherein the concentration of said metal compound in said catalyst is in the range of approximately 2 to 6 weight percent.

* * * * *